United States Patent
Gordon et al.

[19]

[11] Patent Number: 5,867,553
[45] Date of Patent: Feb. 2, 1999

[54] COMPUTED TOMOGRAPHY SCANNER WITH REDUCED POWER X-RAY SOURCE

[75] Inventors: Bernard M. Gordon, Manchester-by-the-Sea; John Dobbs, Hamilton, both of Mass.

[73] Assignee: Analogic Corporation, Peabody, Mass.

[21] Appl. No.: 739,543

[22] Filed: Oct. 30, 1996

Related U.S. Application Data

[63] Continuation of Ser. No. 552,064, Nov. 2, 1995, abandoned.

[51] Int. Cl.⁶ .................................................. G01N 23/00
[52] U.S. Cl. ................................................. 378/4; 378/146
[58] Field of Search ............................... 378/4, 146, 147, 378/62, 137, 156, 157, 13, 12, 19

[56] References Cited

U.S. PATENT DOCUMENTS

| | | | |
|---|---|---|---|
| 4,365,155 | 12/1982 | Oi et al. ...................................... | 378/49 |
| 4,547,893 | 10/1985 | Gordon ........................................ | 378/19 |
| 4,785,354 | 11/1988 | Nakamura et al. .......................... | 378/4 |
| 4,803,711 | 2/1989 | Tsuji et al. ................................. | 378/901 |
| 4,911,189 | 2/1991 | Boomgaarden et al. ................... | 378/151 |
| 5,220,589 | 6/1993 | Gard ........................................... | 378/19 |
| 5,550,886 | 8/1996 | Dobbs et al. ............................... | 378/19 |

*Primary Examiner*—Don Wong
*Attorney, Agent, or Firm*—Lappin & Kusmer

[57] ABSTRACT

The disclosed CT scanner includes an X-ray source and an array of X-ray detectors fixed to a reduced geometry disk which is supported for rotation about an isocenter of the disk. The X-ray source is a reduced power source and a beam hardening filter of reduced size is positioned proximal to the X-ray source so the scanner uses a relatively soft X-ray beam. The scanner further includes circuitry for compensating for non-linearities and channel-to-channel variation in the X-ray detectors.

65 Claims, 4 Drawing Sheets

COMPUTED TOMOGRAPHY SCANNER WITH REDUCED POWER X-RAY SOURCE

CROSS-REFERENCE TO RELATED APPLICATIONS

This Application is a Continuation of U.S. patent application Ser. No. 08/552,064, entitled Computed Tomography Scanner With Reduced Power X-ray Source, filed on Nov. 2, 1995, and assigned to the present assignee, now abandoned.

FIELD OF THE INVENTION

The present invention relates generally to Computed Tomography (CT) scanners used in the medical arts for generating CT images of, for example, human patients. More particularly, the invention relates to an improved CT scanner using a reduced power X-ray source.

BACKGROUND OF THE INVENTION

Computed Tomography (CT) scanners of the third generation type include an X-ray source and an X-ray detector system secured respectively to diametrically opposite sides of an annular-shaped disk. The disk is rotatably mounted within a gantry support so that during a scan, the disk continuously rotates about a rotation axis, commonly referred to as the "Z-axis", while X-rays pass from the source through an object positioned within the opening of the disk to the detector system. The center of the disk, which is intersected by the Z-axis, is commonly referred to as the "isocenter".

The detector system typically includes an array of detectors disposed as a single row in the shape of an arc having a center of curvature at the point, referred to as the "focal spot", where the radiation emanates from the X-ray source. The X-ray source and the array of detectors are positioned so that the X-ray paths between the source and each detector all lie in the same plane (hereinafter the "slice plane " or "scanning plane") which is normal to the rotation axis of the disk. Since the X-ray paths originate from what is substantially a point source and extend at different angles to the detectors, the X-ray paths resemble a fan, and thus the term "fan beam" is frequently used to describe all of the X-ray paths at any one instant of time.

The X-rays incident on a single detector at a measuring instant during a scan are commonly referred to as a "ray", and each detector generates an output signal indicative of the intensity of its corresponding ray. Since each ray is partially attenuated by all the mass in its path, the output signal generated by each detector is representative of the density of all the mass disposed between that detector and the X-ray source (i.e., the density of the mass lying in the detector's corresponding ray path). The output signals generated by the X-ray detectors are generally filtered by a data acquisition system (DAS) to, among other things, improve their signal-to-noise ratio, and the output signals generated by the DAS are commonly referred to as "raw data signals". The raw data signals are normally filtered by a projection filter which converts the raw data signals to projection data signals by logarithmically processing the raw data signals so that each projection data signal is representative of the density of the mass lying in a corresponding ray path. The collection of all the projection data signals at a measuring instant is commonly referred to as a "projection" or a "view". During a single scan, as the disk rotates, a plurality of projections are generated such that each projection is generated at a different angular position of the disk. The angular orientation of the disk corresponding to a particular projection is referred to as the "projection angle".

Using well known algorithms, such as the Radon algorithm, a CT image may be generated from all the projection data signals collected at each of the projection angles. A CT image is representative of the density of a two dimensional "slice", along the scanning plane, of the object being scanned. The process of generating a CT image from the projection data signals is commonly referred to as "filtered back projection" or "reconstruction", since the CT image may be thought of as being reconstructed from the projection data.

CT scanners generally use some form of "beam hardening filter" to "harden" the X-ray beam generated by the X-ray source. The beam hardening filter is generally implemented as a sheet of metal, such as copper or aluminum, disposed between the X-ray source and the patient. Each X-ray photon generated by the X-ray source has a probability of passing through the filter, and this probability increases as the energy of the photon increases. So the filter tends to intercept the lower energy (or "softer") X-rays and thus "hardens" the beam. In the field of CT scanners it is generally believed that it is preferable to use a hard beam because given a certain level of hard X-rays and the same level of soft X-rays, a greater proportion of the soft X-rays have a higher probability of being absorbed by the human body than the corresponding hard X-rays, and thus are less likely to pass through the patient and reach the detectors. In other words, it is currently believed that the use of soft X-rays increases the dose of radiation to which the patient is exposed without significantly contributing to the generation of the CT image. The United States Food and Drug Administration (FDA) has established minimum beam hardness standards CT scanners that operate on human patients must meet.

Further, increasing beam hardness tends to increase the linearity of the X-ray detectors. Accordingly, most prior art CT scanners use a relatively hard beam to improve the linearity of the detectors and thereby simplify the design of the scanner. In fact, most prior art CT scanners use a relatively high power (e.g., 120 kV at 100 to 350 mA) X-ray source and also use a relatively thick (e.g., 0.008 inches of copper) beam hardening filter which hardens the beam by significantly more than is required by the FDA. The combination of a high power X-ray source and a thick beam hardening filter simplifies the design of the CT scanner, however, it is wasteful of X-ray power and increases the overall power requirements of the scanner.

Another factor tending to increase the X-ray power used by prior art CT scanners relates to the distance between the focal spot and the isocenter of the disk. Since the intensity of an X-ray beam decreases with the square of the distance from the X-ray source, the power used in the X-ray source is determined in part by the distance between the focal spot and the isocenter. (This factor is generally described in terms of the distance between the focal spot and the isocenter rather than in terms of the distance between the focal spot and the detectors because during a scan the patient is generally located at or near the isocenter, and while it is generally possible to increase the X-ray energy received by a detector by increasing the size of the detector, it is only possible to increase the X-ray energy at the isocenter (i.e., at the patient) by increasing the power of the X-ray source or by decreasing the distance between the focal spot and the isocenter.)

Designing a CT scanner for reduced X-ray power consumption therefore suggests placing the isocenter as close as is possible to the X-ray source. However, other competing design criteria require increasing the spacing between the X-ray source and the isocenter. For example, at a minimum, the isocenter must be spaced apart from the X-ray source at least far enough to allow a patient to be comfortably positioned between the X-ray source and the detectors. A phenomenon generally known as "Z-axis beam shifting" places an even greater requirement on the spacing between the X-ray source and the isocenter. Beam shifting relates to movement of the focal spot (i.e., the point from which the X-rays emanate) relative to the isocenter (or the detectors) during a scan. The generation of X-rays produces localized heat which can cause thermal expansion of components of the X-ray source, and this thermal expansion can in turn cause the focal spot to shift relative to the isocenter during a scan. This shift is generally referred to as Z-axis beam shifting because most X-ray sources are configured so that the majority, if not all, of the shift occurs in a direction that is parallel to the Z-axis (i.e., the rotation axis of the scanner disk). Since the Radon algorithm assumes that the relative positions of the X-ray source and the detectors remain constant during a scan, it is important to minimize the effects of any Z-axis beam shifting. In prior art CT scanners, the most common method of minimizing this effect is to increase the spacing between the X-ray source and the collimator used to form and shape the beam, and thereby reduce the angular shift between the focal spot and the detectors caused by any Z-axis translation of the focal spot. Lengthening the distance between the focal spot and the collimator necessarily increases the distance between the focal spot and the isocenter since a certain amount of space is required to receive a patient. In the field of CT scanners, it is generally believed that if the focal spot is not spaced at least 510 mm apart from the isocenter of the disk, the collimator must be placed too closely to the focal spot such that errors caused by Z-axis beam shifting will become too severe. However as stated above, any increase in this distance necessitates a corresponding increase in the power applied to the X-ray source. Prior art CT scanners which increase this spacing therefore do so at the cost of increasing their X-ray power requirements. Thus, such prior art scanners expose the patient to higher levels of X-radiation, since increasing the spacing between the source and isocenter to accommodate a greater spacing between the focal spot and a collimator necessitates generating higher energy X-rays.

In addition to reducing the distance between the X-ray source and the isocenter, X-ray power consumption can be reduced by using high efficiency detectors, such as solid state detectors (e.g., cadmium tungstate detectors). However, many prior art CT scanners use less efficient, gas tube detectors, such as Xenon (Xe) detectors, because the response of such detectors tends to be more uniform than the response of high efficiency detectors. In particular, such low efficiency detectors detect photons more uniformly in the Z-axis direction than do high efficiency detectors. Therefore, prior art CT scanners which use high efficiency detectors also use a large spacing between the focal spot and the collimator (and as a result a large spacing between the focal spot and the isocenter) so as to minimize the effect of any Z-axis beam shifting, resulting in a sacrifice of much of the power savings achieved by the high efficiency detectors. Similarly, many prior art CT scanners which use reduced spacing between the focal spot and the collimator and thus a reduction in the spacing between the focal spot and the isocenter, at the 510 mm spacing for example, also use low efficiency detectors to minimize the effect of any Z-axis beam shifting, and thereby sacrifice much of the power savings achieved by the reduced geometry.

As was stated above, prior art CT scanners also normally use a DAS to, among other things, improve the signal-to-noise ratio of the output signals generated by the X-ray detectors. However, prior art DASs are often implemented using an integrating filter which does not significantly improve the signal-to-noise ratio of the detector output signals. Therefore, prior art scanners typically use high intensity X-ray beams to insure that the signal-to-noise ratio of the detector output signals is sufficiently high to guarantee generation of accurate CT images.

In general, prior art CT scanners have been designed to improve the accuracy of the generated CT images at the expense of requiring increased X-ray power levels. There is therefore a need for a CT scanner which generates high quality CT images and also has reduced X-ray power requirements. There is also a need for a CT scanner which generates high quality CT images while exposing the patient to lower levels of radiation.

OBJECTS OF THE INVENTION

It is an object of the present invention to substantially reduce or overcome the above-identified problems of the prior art.

Another object of the present invention is to provide an improved CT scanner with a X-ray source that operates at a reduced power level.

Still another object of the present invention is to provide an improved CT scanner with an X-ray source including a cathode and an anode where the rated potential between the anode and cathode can be on the order of 120 kV and the rated current between the anode and cathode can be on the order of 50 mA for a rated power of 6 kVA, substantially less than the 12 kVA or higher required of currently available CT scanners.

And another object of the present invention is to provide an improved CT scanner having a reduced geometry.

And yet another object of the invention is to provide an improved CT scanner having a disk which defines an isocenter and an X-ray source which generates X-rays that emanate from a focal spot, where the focal spot is spaced apart from the isocenter by a distance required for the comfort of the average sized patient, a distance on the order of 475 mm, which is smaller than the current, commercially available, minimum distance of 510 mm so as to reduce the power requirements of the scanner.

And still another object of the present invention is to provide a CT scanner which includes high efficiency, solid state X-ray detectors.

And yet another object of the present invention is to provide an improved CT scanner which includes a beam hardening filter of reduced thickness.

And another object of the present invention is to provide an improved CT scanner which uses a softer X-ray beam.

And still another object of the present invention is to provide an improved low power CT scanner comprising a DAS including best estimate filters for use in generating raw data signals.

And yet another object of the present invention is to provide an improved CT scanner including circuitry for compensating for non-linearities and channel-to-channel variations in and among the various detectors and signal processing channels, as well as for other non-linearities and variations in the channels of the scanner.

And another object of the present invention is to provide an improved CT scanner including circuitry for compensating for channel-to-channel variations in the response of and among the detectors caused by factors such as radiation damage, zero offset and variation in gain as a function of temperature.

SUMMARY OF THE INVENTION

These and other objects are provided by an improved CT scanner having a disk supported for rotation about an isocenter of the disk and X-ray components arranged as a system of reduced geometry. The preferred scanner described in connection with the drawings is of the third generation type, although it should be understood that many of the aspects of the present invention can be applied to other types of scanners, such as fourth generation machines. The preferred scanner described herein includes an X-ray source and an array of X-ray detectors fixed to the disk. The X-ray source generates X-rays so that the X-rays emanate from a focal spot, and the X-ray source is preferably mounted to the disk so that the focal spot is spaced on the order of 475 mm away from the isocenter.

In one aspect of the invention, the X-ray source includes a power source adapted to operate at a relatively reduced level of power, and the scanner includes a beam hardening filter of reduced thickness. In accordance with this aspect of the invention, the scanner uses a relatively soft X-ray beam.

In accordance with another aspect of the invention, the scanner includes circuitry for compensating for nonlinearities and variations in and among the X-ray detectors and signal processing channels.

Still other objects and advantages of the present invention will become readily apparent to those skilled in the art from the following detailed description wherein several embodiments are shown and described, simply by way of illustration of the best mode of the invention. As will be realized, the invention is capable of other and different embodiments, and its several details are capable of modifications in various respects, all without departing from the invention. Accordingly, the drawings and description are to be regarded as illustrative in nature, and not in a restrictive or limiting sense, with the scope of the application being indicated in the claims.

BRIEF DESCRIPTION OF THE DRAWINGS

For a fuller understanding of the nature and objects of the present invention, reference should be made to the following detailed description taken in connection with the accompanying drawings in which the same reference numerals are used to indicate the same or similar parts wherein.

DETAILED DESCRIPTION OF THE DRAWINGS

Figure 1:
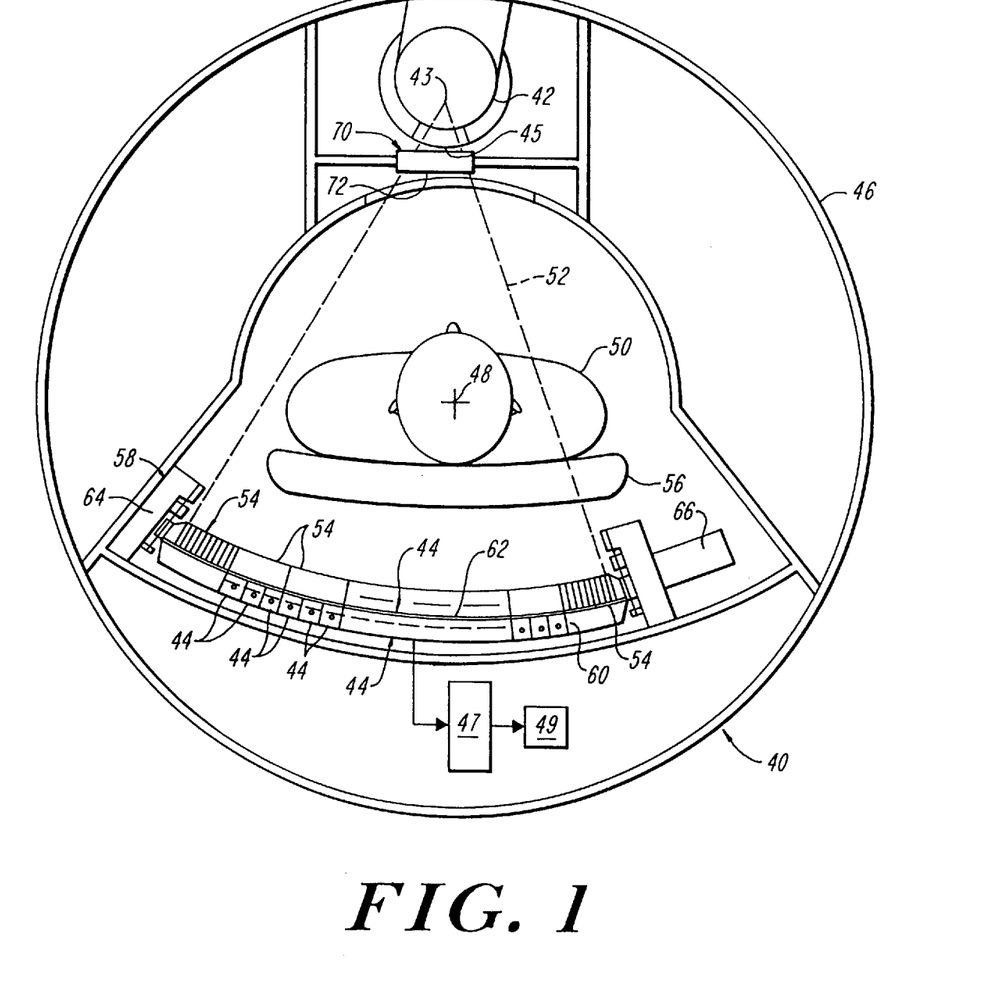
FIG. 1 is an axial view of a rotatable disk of a CT scanner constructed according to the invention.

FIG. 1 illustrates a disk assembly of a CT scanner 40 incorporating the principles of the present invention. Scanner 40 is designed for increased X-ray power efficiency and reduced overall power requirements. As will be discussed further below, scanner 40 uses a X-ray source adapted to operate at a reduced level of power, and a softer X-ray beam than has been used in commercially available prior art machines. While the conventional wisdom in the field of CT scanners has taught that it is preferable to use harder X-ray beams, the applicants have unexpectedly discovered that use of a softer X-ray beam actually improves the clarity and contrast of the generated CT images if careful calibration and control is practiced.

Figure 2:
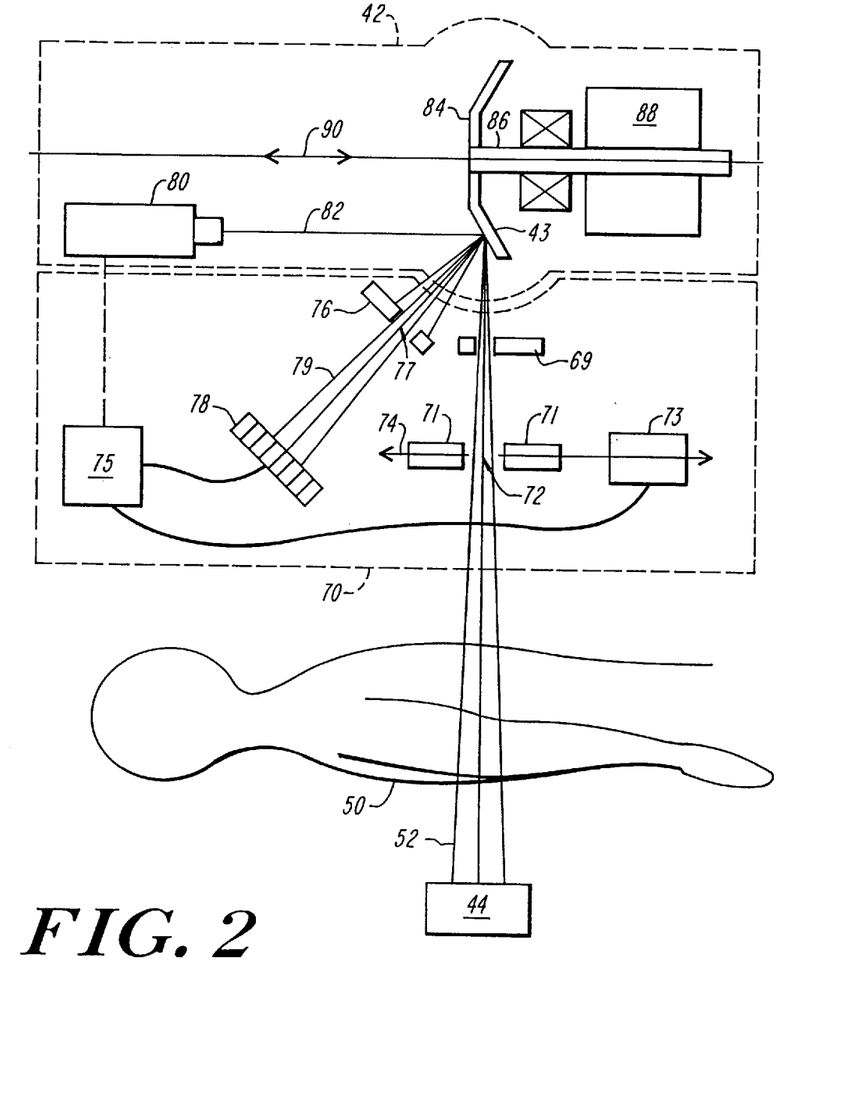
FIG. 2 is a partially sectional side view of the CT scanner shown in FIG. 1, showing the X-ray source assembly and the Z-axis tracking system in detail with the fan beam partially broken away.

Scanner 40 also has a reduced geometry which contributes to the improved X-ray power efficiency. More particularly, scanner 40 includes an X-ray source 42 and an array of detectors 44, each of which are mounted on an apertured disk 46. A beam hardening filter 45 is mounted to the outer surface of X-ray source 42. The disk is supported by a gantry (not shown) and is configured to rotate about a Z-axis, or rotation axis, so as to rotate the source 42 and detectors 44 around an object 50 that extends through the central opening of the disk during a CT scan. The rotation axis is normal to the view shown in FIG. 1 and intersects an isocenter 48 of the disk. Object 50 may be part of a live human patient such as the head or torso. When activated, source 42 emits X-rays from a focal spot 43, and a portion of these emitted X-rays pass through beam hardening filter 45. A beam shaping and monitoring system 70, described more fully in connection with FIG. 2, is positioned relative to the filter 45 so as to form a fan-shaped beam 52 which passes through object 50 (when the latter is positioned at or near the isocenter 48 with the fan beam) and is incident on detectors 44. Fan beam 52 defines a scanning plane that is normal to the rotation axis and that intersects the rotation axis at the isocenter 48 of disk 46. An array of anti-scatter plates 54 is preferably disposed adjacent to detector array 44 between the array and object 50 to substantially prevent the detectors from sensing scattered X-rays. A DAS, generally indicated at 47, collects the data generated by the detector array and generates the raw data signals, which are in turn applied to computer 49. Computer 49 processes the raw data signals which can be transmitted from the disk (i) to a monitor for displaying the resulting CT image (not shown), preferably positioned near the disk and/or (ii) to memory for storing the image data for subsequent display, (iii) to a processor for subsequent processing, and/or (iv) to a remote site, and/or (v) some other device and/or location. A suitable transmission and reception system is described in U.S. patent application Ser. No. 08/174,664 filed Dec. 28, 1993 in the names of Bernard M. Gordon et al., and entitled Apparatus for Transferring Data to and from a Moving Device, and assigned to the present assignee, now U.S. Pat. No. 5,577,026, issued Nov. 19, 1996.

In accordance with one aspect of the present invention, and in a preferred embodiment, source 42 and disk 46 are configured so that focal spot 43 is positioned more closely to isocenter 48 than was thought practical in the prior art. In considering the design of the system of the present invention, it is desirable to make this distance as small as practical utilizing a very wide angle of x-ray emanating from the focal spot, and to take advantage of the fact that the intensity of x-rays decreases as a function of the square of the distance from the focal spot to the part of the body under observation. Thus, the closer the body is to the x-ray source, the lower the power required to generate sufficient x-rays for a CT scan. Therefore, one design goal of the present invention is to minimize the distance between the focal spot and isocenter. However, a major constraint on minimizing this distance is the opening of the gantry, sized to receive the object to be scanned. In one preferred embodiment, the gantry opening is 60 cm which is sized to accommodate an average sized person, the field of view is 46 cm, the focal spot 43 is spaced apart from isocenter 48 by a distance on the order of 475 mm, and focal spot 43 is spaced apart from each detector in array 44 by a distance on the order of 845 mm. In other embodiments the spacing between focal spot 43 and isocenter 48 may be less than the 510 mm and on the order of 450 mm and still receive the average sized patient. Obviously, machines which are designed for use on smaller objects (on arms and/or legs, for example) would have even smaller gantry openings with the distance between the focal spot and the isocenter being accordingly reduced. The 475 mm spacing is provided in the preferred machine since it allows the X-ray source 42 to operate at reduced power levels and yet comfortably accommodates an average sized person as the scanned object. Also in the preferred embodiment, the array 44 of detectors is implemented using high efficiency, solid state, detectors such as cadmium tungstate detectors (each of which typically contains a silicon photodiode and a cadmium tungstate scintillator for improving the efficiency of the detector). The high efficiency of these detectors allows X-ray source 42 to operate at even further reduced power levels. In one preferred embodiment, detector array 44 is implemented using 384 detectors covering an arc of 48 degrees, although the number and angle can vary.

The preferred form of beam shaping and monitoring system 70, is more fully described in copending U.S. patent application Ser. No. 08/343,240 filed Nov. 22, 1994, entitled X-ray Focal Spot Movement Compensation System, now U.S. Pat. No. 5,550,886, issued Aug. 27, 1996 and U.S. patent application Ser. No. 08/343,248 filed Nov. 22, 1994 in the names of John Dobbs and Hans Weedon, entitled Normalization of Tomographic Image Data abandoned in favor of continuation application U.S. patent application Ser. No. 08/677,192, filed Jul. 9, 1996, and issued on Oct. 21, 1997 as U.S. Pat. No. 5,680,427, both assigned to the current assignee of the present invention, and incorporated herein by reference. The preferred system 70 includes a detector for sensing any movement of the focal spot in the Z-axis direction and a moveable collimator for maintaining the beam in the correct Z-axis position at the isocenter relative to the array of detectors. Thus, the system 70 operates to correct for any movement of the focal spot 43 in the Z-axis direction so that the scanner can operate independently of the spacing between the focal spot 43 and collimator of the system 70. This allows for the spacing between the focal spot and the isocenter to be smaller than the 510 mm of the prior art system, and also allows for the use of high efficiency detectors which are otherwise sensitive to shifts of the focal spot in the Z-axis direction.

Briefly, as shown in detail in FIG. 2, system 70 includes a precollimator 69 and collimator 71 defining at least one aperture 72 shaped to form fan beam 52. If focal spot 43 shifts during a scan as is described in greater detail hereinafter, then system 70 tracks the shift and translates the collimator 71 so as to insure that fan beam 52 is always incident on the same portion of detector array 44.

As shown in FIG. 2, source 42 includes an electron beam generator, or cathode, 80 which emits an electron beam 82 that is incident on anode 84. Preferably, anode 84 is a tungsten disk and is rotatably mounted to a shaft 86. When electron beam generator 80 is active, a motor 88 preferably rotates shaft 86 so as to rotate anode 84 to facilitate cooling and to prevent the electron beam 82 from damaging anode 84. Since the generation of X-rays produces heat, shaft 86 tends to thermally expand along an axis 90 parallel to the Z-axis when source 42 is active. Shaft 86 then tends to contract when it cools. This expansion and contraction in turn causes shifts of focal spot 43 along an axis that is parallel to the Z-axis.

The beam tracking and monitoring system 70 includes a second collimator 76 with an aperture 77 for forming a second beam 79, off-axis from beam 52. The position of beam 79 is monitored by monitoring detector 78. When the focal spot moves in the Z-axis direction, the beam 79 shifts relative to the detector 78. The output of detector 78 is a function of the position of the beam 79, and thus provides an indication of the position of the focal spot 43. The detector output is applied to controller 75, which in turn controls a stepping motor 73 translatably coupled to a collimator 71. Under the control of controller 75, motor 73 selectively translates plate 71 along an axis 74 which is parallel to the Z-axis and positions the collimator 71 in a position as a function of the position of the focal spot as sensed by the detector 78. When detector 78 detects a shift of focal spot 43, controller 75 operates motor 73 to shift collimator 71 by a corresponding amount so that the fan beam 52 remains incident on the same portion of detector array 44. System 70 thus reduces the errors caused by Z-axis beam shifting and allows the collimator 71 to be placed very close to the focal spot 43. System 70 therefore permits focal spot 43 to be positioned a distance on the order of 475 mm away from the isocenter 48 (thereby allowing X-ray source 42 to operate at reduce power levels) without introducing unacceptable errors caused by Z-axis beam shifting. In other embodiments, focal spot 43 may be positioned even more closely to the isocenter 48.

Scanner 40 also uses an "asymmetric" fan beam 52 which allows focal spot 43 to be positioned more closely to the isocenter than would be possible with a symmetric fan beam. As shown in FIG. 1, fan beam 52 is not symmetrically disposed about the isocenter 48, but rather a greater percentage of the fan beam is incident on the detectors to the left of the isocenter as shown. As is known in the art, use of such an asymmetric fan beam reduces the amount of radiation delivered to the periphery of the patient and also allows focal spot 43 to be located closer to the isocenter than would be possible with a symmetric fan beam without decreasing the field of view of the scanner. The combination of the high efficiency detectors of array 44, the beam tracking and monitoring system 70, and the asymmetric fan beam shown in FIG. 1 allows the focal spot 43 to be positioned closer to the isocenter 48 than was thought possible in the prior art (i.e., on the order of 475 mm away from the isocenter) which in turn allows source 42 to operate at reduced power levels.

X-ray source 42 is preferably a low power source. The minimum power rating of the power source of the machine is a function of the time of the scan, as well as the desired signal-to-noise ratio. That is the noise increases as a function of the square root of the number of photons detected. The number of detected photons is improved by the use of highly efficient detectors and the reduction in the distance between the focal spot and the isocenter. In one preferred embodiment the rated potential between cathode 80 and anode 84 is on the order of 120 kV (kilovolts) (e.g., anode 84 is maintained at 60 kV and cathode 80 is maintained at −60 kV) and electron beam 82 provides approximately 50 mA (milliamperes) of current to anode 84, thereby providing a power rating of 6 kW, which is substantially less than the 12 kWs and higher required by prior art commercially-available machines. Scanner 40 preferably completes a single scan in approximately two seconds (i.e., disk 46 rotates 360 degrees in two seconds) so the scanner uses approximately 100 mAs (milli-ampere-seconds) per scan, whereas most prior art CT scanners use about 300–400 mAs per scan. The power rating could go lower, and in some rare applications the embodiment described could operate on the order of 1 kW for a 2 second scan.

With regard to a beam hardening filter 45, prior to the present invention it has been conventional wisdom to harden the beam to make the x-ray spectrum of the x-ray beam more monochromatic. However, in accordance with the present invention, beam hardening filter 45 (shown in FIG. 1) implements at least the minimum amount of filtering permitted by the United States Food and Drug Adminstration (FDA), but allows significantly more soft X-rays to be transmitted in beam 52 than are normally found in die commercially available machines of the prior art. In the preferred embodiment, beam hardening filter 45 is implemented as a sheet of copper that is on the order of 0.003 inches thick, although filter 45 may of course be implemented using an equivalent or nearly equivalent thickness of other metals such as iron, aluminum or titanium or other metals having a relatively low atomic number. In general the amount of filtration added is a function of the particular type of x-ray source used, and is affected by such design factors as anode angle, and the material thickness of the insert window, oil and external window through which the x-rays photons pass. In the embodiment described the minimum thickness to satisfy FDA requirements is on the order of 0.002 inches of copper, although it will be appreciated that this minimum can vary determined on the x-ray source and design factors such as those mentioned. A preferred method of selecting the thickness of beam hardening filter 45 will be discussed below. This combination of a thin beam hardening filter and a low power source exposes the patient to permissible dose levels without reducing the quality of the CT images and in fact has unexpectedly provided an improved CT image.

Figure 3:
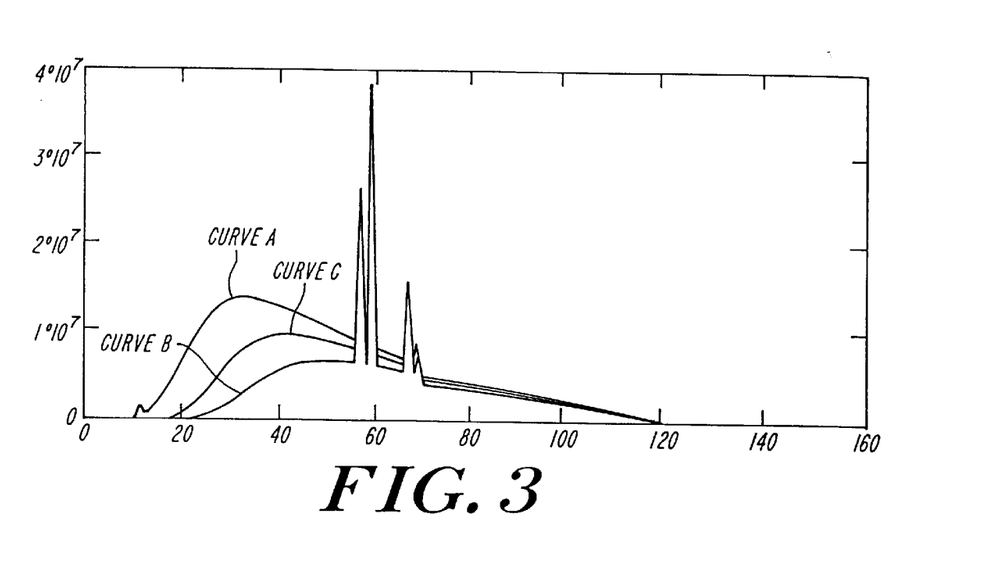
FIG. 3 is a graph illustrating a typical energy spectrum of the X-ray beam used in the CT scanner shown in FIG. 1 alone, with a prior art beam hardening filter and with the X-ray filter designed in accordance with one aspect of the present invention.

FIG. 3 shows three curves, curves A, B and C, which respectively illustrate the spectral distribution of beam 52 under three different conditions. In FIG. 3, the x axis represents X-ray photon energy levels in keV (kilo-electronvolts), and the y axis represents the number of emitted X-ray photons in the beam. Curve A illustrates a typical spectral distribution of an X-ray beam when the beam is unfiltered. Curve B illustrates the spectral distribution of an X-ray beam passed with a beam hardening filter made from a sheet of copper that is 0.008 inches thick and therefore illustrates a typical spectrum of a filtered beam used in a prior art scanner, Use of such a filter is based on what is believed to be the ideal spectrum, a single line spectrum monochromatic spectrum, Prior to the present invention use of a monochromatic spectrum was believed desirable since it was believed a broad spectrum would provide less information. For descriptive purposes herein, this distribution as well as the spectral distributions of beam hardening filters known in the prior art, are collectively referred to as the "standard" filtered spectral distribution. Curve C illustrates the spectral distribution of an X-ray beam passed by a preferred filter made in accordance with the present invention and comprises a sheet of copper that is 0.003 inches thick. In accordance with the present invention, the actual lower amount of filtering is determined by a tradeoff of the desired dosage level provided to the patient and, as the resolution of the image. Obviously if no filtering were provided, the patient would be exposed to more softer x-rays than desired. Surprisingly, one achieves better resolution by letting through more soft x-rays through to the body being scanned. This in turn allows operation at lower power. Curve C thus illustrates the preferred spectrum of fan beam 52 which is used in scanner 40. Those skilled in the art will appreciate that in prior art scanners the unfiltered beam, represented by curve A, is generated using a higher power X-ray source than is used in scanner 40, and therefore there is a difference in scale between the standard filtered spectral distribution, represented by curve B, and the preferred spectrum of fan beam 52, represented by curve C, which is not shown in FIG. 3. Clearly, curve C has a considerably "softer" spectrum than does curve B. Soft X-rays are considered those emitted at the lower energy levels, and the distinction between soft and hard X-rays is usually considered to occur somewhere between 40 keV and 60 keV. Thus, for purposes of describing the distinctions between soft and hard X-rays, the average value of 50 keV is used to facilitate the description of the filter 45 of the present invention, so that energy levels below or equal to 50 keV are considered soft X-rays, while energy levels above 50 keV are considered hard X-rays.

As illustrated by curves A, B and C, as with the prior art filter made of a sheet of copper 0.008 inches thick, the spectrum of beam 52 using the filter 45 including a sheet of copper of 0.003 inches preferably contains relatively few or no photons having an energy level less than about 20 keV since such photons are unlikely to pass through a patient and reach one of the X-ray detectors, and therefore inclusion of such photons would increase the dose of radiation delivered to the patient without adding to the clarity of the CT image. However, the spectrum of fan beam 52 as filtered by filter 45 as illustrated by curve C preferably includes a larger number of photons having energy levels in the range of about 20 keV to about 50 keV, the so-called "soft X-rays" than provided in the standard filtered spectral distribution, as exemplified by curve B. Inclusion of a larger number of such photons is desirable since, as will be discussed further below, the absorption characteristics of these photons appears to vary more significantly with density making it possible to distinguish similar types of tissue (e.g., the absorption characteristics in this energy range is different for white and grey matter) and therefore these photons contribute greatly to the contrast of the reconstructed CT images. Preferably, the spectrum of fan beam 52 with filter 45 includes a peak between about 35 and about 50 keV, and more preferably, between about 35 and about 45 keV which is substantially nonexistent with the prior art filter shown by curve B of FIG. 3. Further, the portion of the spectrum above 50 keV shows a slight increase of hard X-rays with the 0.003 inch thick copper filter when compared to the prior art 0.008 inch thick copper of the prior art (except for the spikes shown in the Fig. which remain substantially unchanged. It is clear that a greater proportion of soft X-ray photons have been added to the beam.

The use of a greater proportion of softer X-ray photons allows scanner 40 to generate CT images of increased clarity. This may be understood by considering the well known relationship between the intensity of an X-ray beam and the amount of absorbing media through which the beam has passed. This relationship is shown in the following Equation (1):

$$I = I_0 e \int_0^L \mu dL \tag{1}$$

in which $I_O$ is the intensity of the beam prior to entering the absorbing media, L is the length of the media through which the beam has passed, $\mu$ is the coefficient of absorption for the media, and I is the intensity of the beam after passing through the media. The coefficient of absorption for a given medium is not a constant and is instead a function of X-ray energy, and the coefficients for different types of body tissue (e.g., fat, muscle, white and gray matter) are more different at low energies (e.g., between about 20 keV and 50 keV) than they are at high energies. There is therefore more information in low energy photons since the these photons are more sensitive to the differences between different types of body tissue. Therefore, lower energy (i.e., softer) beams are better at discriminating between different types of body tissue and allow generation of higher quality CT images with better contrast.

While the use of a low energy beam is preferred because it improves the efficiency and reduces the power requirements of scanner 40, and while the use of a softer X-ray beam is preferred because it allows generation of an improved CT image, these factors also introduce complexities into the design of scanner 40. For example, since the X-ray beam is a low intensity beam, the outputs of the detectors in array 44 generally have a correspondingly low signal-to-noise ratio and scanner 40 preferably filters these outputs in a manner that significantly improves their signal-to-noise ratio. Also, use of the low intensity beam increases the sensitivity of scanner 40 to variations in the gains of the detectors, and scanner 40 therefore preferably compensates for these variations. Further, as is well known, the response of an X-ray detector generally tends to become increasingly linear as the hardness of the beam increases. Since scanner 40 uses a relatively soft beam, the response of the detectors in array 44 tends to be non-linear, and scanner 40 preferably compensates for these non-linearities. These functions are preferably performed by DAS 47 and computer 49.

Figure 4:
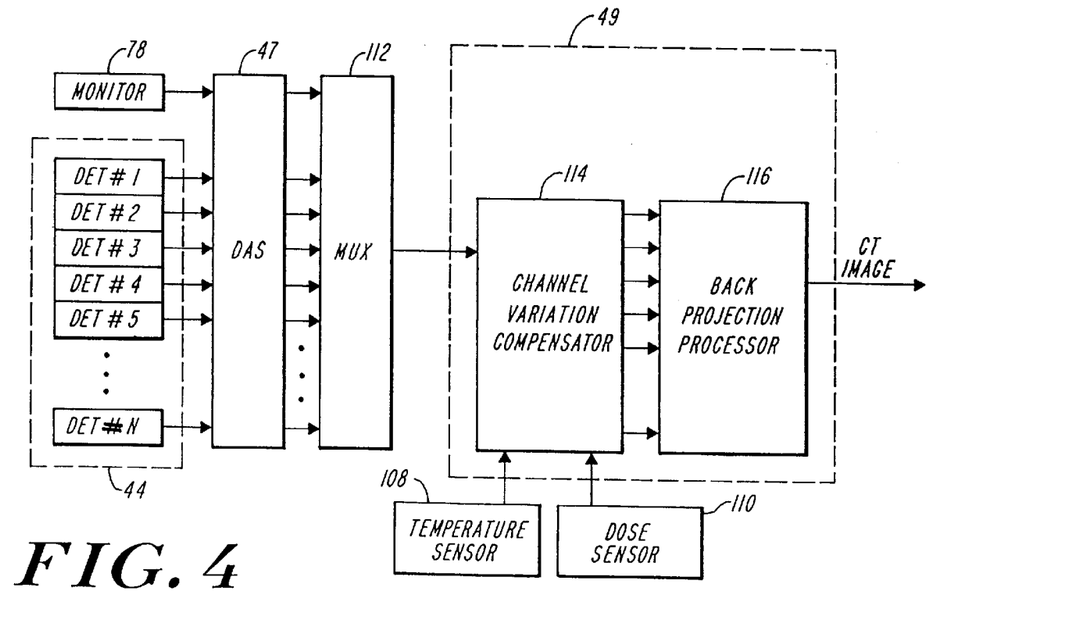
FIG. 4 is a block diagram of the DAS and computer used in the CT scanner shown in FIG. 1.

FIG. 4 shows a block diagram illustrating the connection between DAS 47 and computer 49. The detector array 44 contains N detectors, and as stated above, in one preferred embodiment N is equal to 384, although this number can vary. DAS 47 and computer 49 also each have N channels, each channel corresponding to one detector, although the number of channels can be reduced by using a multiplexer as is well known. In general, all the channels function in a substantially similar fashion, and any discussion of one channel is therefore illustrative of all of the channels.

The N detectors generate N output signals which are applied to the inputs of DAS 47. Monitor detector 78, which also is used to measure the intensity of the X-ray beam proximal to the source 42, also generates an output signal which is applied to DAS 47. Monitor detector 78 is preferably implemented to include a silicon photodiode. Since the intensity of the X-ray beam is much higher at monitor detector 78 than at detector array 44 (because monitor detector 78 is much closer to the source 42), monitor detector 78 need not be as efficient as the detectors of array 44 and in the preferred embodiment monitor detector 78 does not contain a high efficiency scintillator, such as a cadmium tungstate scintillator, although of course in other embodiments, monitor detector 78 may contain such a scintillator. DAS 47 preferably filters the detector and monitor detector output signals to improve their signal-to-noise ratio, and generates raw data signals which are applied to the inputs of a multiplexer 112. The latter preferably transmits N raw data signals and the monitor detector output signal to computer 49 via a single multiplexed connection provided by multiplexer 114, and thereby reduces the number of connections between DAS 47 and computer 49. However, in other embodiments multiplexer 112 may be eliminated and the raw data signals generated by DAS 47 may be applied directly to computer 49. Scanner 40 may additionally contain a temperature sensor 108 and a dose sensor 110, each of which generates an output signal that is applied to computer 49. Computer 49 then processes the N raw data signals, the output of the monitor detector 78 and the outputs of sensors 108, 110 so as to compensate for non-linearities in the channels as well as channel to channel variations in scanner 40 and then generates CT images from the processed data.

DAS 47 preferably contains N best estimate filters of the type described in U.S. Pat. No. 4,547,893, entitled CONTINUOUS WAVE FAN BEAM TOMOGRAPHY SYSTEM HAVING A BEST-ESTIMATING FILTER, issued to Bernard M. Gordon, assigned to the assignee of the present invention, and which is hereby incorporated by reference, each for filtering the output of a corresponding detector of array 44. Briefly, each best estimate filter has a frequency range that is chosen to match the mechanical geometry of scanner 40. The output of each best estimate filter can be periodically read independently of when each projection reading is to be determined, and the values of the detected radiation of each projection reading estimated from the filter outputs. Each detector in array 44 thus generates an output signal which is applied to a corresponding best estimate filter in DAS 47. Each best estimate filter typically improves the signal-to-noise ratio of the corresponding detector output signal by about fifteen percent. This boost in signal-to-noise ratio improves the overall efficiency level of scanner 40 and allows the X-ray source 42 to operate at reduced power levels. The N best estimate filters each generate a raw data signal, and DAS 47 preferably converts these N raw data signals to digital signals and applies the N digital signals to computer 49 via multiplexer 112. DAS 47 may also contain a best estimate filter for boosting the signal-to-noise ratio of the output of monitor detector 78, and also contains circuitry for converting the output of this best estimate filter to a digital signal and for applying this signal to computer 49.

Computer 49, which may be implemented as an array processor, contains a channel variation compensator 114 and a back projection processor 116. As those skilled in the art will appreciate, compensator 114 and back projection processor 116 may each be implemented in special purpose hardware or as a software module running on a digital computer such as an array processor.

The input to the back projection processor 116 is preferably a set of N signals each of which is representative of $\int \mu dL$ over the corresponding ray paths, where these quantities are as defined in Equation (1), and where the jth signal is representative of $\int \mu dL$ as measured by the jth detector in array 44. Equation (2), which is derived simply by rearranging Equation (1), provides a formula for calculating $\int \mu dL$:

$$\int_0^L \mu dL = -\ln\left(\frac{I}{I_0}\right) \quad (2)$$

in which $I_O$ is the intensity of the X-ray beam at the source 42, I is the intensity of the X-ray beam at the jth detector in array 44, and L is the length of the media through which the beam has passed. The absorbing media through which the beam has passed are the portion of the patient and the air (which only absorbs a negligible amount of X-ray energy) disposed between the source and the jth detector.

Since the quantities I and $I_O$ are not directly available to computer 49, compensator 114 may implement an approximation of Equation (2), and generate an estimate for each channel of the quantity $\int \mu dL$. One such approximation is described in the following Equation (3) in which E:j is the estimate of the quantity $\int \mu dL$ for the jth channel:

$$E:j = \int_0^L \mu dL = -\ln\left(\frac{I}{I_0}\right) \approx -\ln\frac{\left(\frac{d:j_p}{m_p}\right)}{\left(\frac{d:j_{np}}{m_{np}}\right)} \quad (3)$$

wherein $d:j_{np}$ is the raw data signal in the jth channel (i.e., the raw data signal generated from the jth detector's output signal) when no patient is present (i.e., when there is nothing but air between the source and the jth detector), $m_{np}$ is the raw data signal corresponding to the output of monitor detector 78 at a point in time close to when $d:j_{np}$ was measured (i.e., preferably within a few microseconds), $d:j_p$ is the raw data signal in the jth channel measured during a given projection of a scan (i.e., when a patient is present), and $m_p$ is the raw data signal corresponding to the output of monitor detector 78 at a point in time close to when $d:j_p$ was measured. Since the denominator of the right side of Equation (3) (i.e., $d:j_{np}/m_{np}$), which is referred to as the "gain" of the jth detector, does not depend on the patient, this quantity may be calculated at a time when no scan is being performed. It is convenient to calculate the gain of each channel once a day, for example when the scanner 40 is initially powered up, and to store the gains for use throughout the day, although the gains can of course be calculated at other times as well.

The quantity $$\frac{\left(\frac{d:j_p}{m_p}\right)}{\left(\frac{d:j_{np}}{m_{np}}\right)}$$

which is used in Equation (3) is referred to as the normalized intensity of the jth channel and provides a close approximation to the quantity $I/I_O$ as measured in the jth channel. So in one embodiment, compensator 114 implements Equation (3) and generates N estimates E:j, each of which is the negative logarithmn of the normalized intensity that was measured in one of the N channels of scanner 40.

However, in the preferred embodiment, rather than implementing the approximation described in Equation (3), compensator 114 additionally provides compensation for several factors which can affect the accuracy of scanner 40 when generating the estimates. In one preferred embodiment, compensator 114 compensates for the "zero offset" of each detector (i.e., the output of each detector when no X-rays are incident on the detector) when generating the estimates. Compensator 114 also preferably compensates for the temperature of the detectors when generating the estimates since the gains of the detectors sometimes vary in a channel dependent fashion according to temperature. Compensator 114 also preferably compensates for a factor known as "radiation damage" when generating the estimates. As is well known, the gain of an X-ray detector sometimes varies according to the dose of radiation to which the detector has been recently exposed, and the term "radiation damage" refers to this variation in gain. Since radiation damage is generally not permanent (i.e., after experiencing radiation damage, if a detector is not exposed to radiation for a period of time, the gain of the detector will eventually substantially return to an original "undamaged" nominal value), compensator 114 considers the dose of radiation to which each detector has been exposed as well as the time that the exposure occurred when compensating for radiation damage. In one preferred embodiment, compensator 114 generates the estimates E:j according to the following Equation (4):

$$E:j = \int_0^L \mu dL = -\ln\left(\frac{I}{I_0}\right) \approx$$

$$-\ln\left\{\frac{\left(\frac{d:j_p - d:j_{p0}}{m_p - m_{p0}}\right)}{\left(\frac{d:j_{np} - d:j_{np0}}{m_{np} - m_{np0}}\right)}(Temp:j)(Rad\ Dam:j)\right\} \quad (4)$$

in which $d:j_{pO}$ is the zero offset in the jth detector (i.e., the raw data signal in the jth channel when the X-ray source 42 is inactive) measured at a time close to when $d:j_p$ was measured (i.e., preferably measured within a few seconds of $d:j_p$), $m_{pO}$ is the zero offset of monitor detector 78 measured at a time close to when $m_p$ was measured, $d:j_{npO}$ is the zero offset in the jth detector measured at a time close to when $d:j_{np}$ was measured, $m_{npO}$ is the zero offset of monitor detector 78 measured at a time close to when $m_{np}$ was measured, Temp:j is a gain correction factor correcting for variation in the gain of the jth detector as a function of temperature, and Rad Dam:j is a gain correction factor correcting for variation in the gain of the jth detector as a function of radiation damage.

Preferably, the N factors Temp:j for the corresponding N number of channels are determined experimentally by characterizing each of the N detectors at different temperatures (i.e., the variation in gain from a nominal value of each detector is measured at many different operating temperatures) and this data is assembled, using known statistical techniques, to generate a curve for each of the N detectors relating the operating temperature to the gain variation experienced by that detector at that operating temperature. These curves are then stored in a set of N temperature variation tables, one table for each of the N detectors, and these tables are stored in compensator 114, preferably using a bank of look up tables. In operation, temperature sensor 108 provides a signal to compensator 114 representative of the temperature of the detector array 44 and compensator 114 applies this signal to the temperature variation tables to generate the N temperature correction factors Temp:j. Similarly, the factors Rad Dam:j are determined experimentally by characterizing each of the N detectors for many different doses of radiation delivered over many different time intervals. This data is used to generate N radiation damage tables which are stored in compensator 114, preferably in a bank of look up tables. In operation, dose sensor 110 applies N signals to compensator 114, each of the signals being representative of the dose of radiation to which one of the detectors has been exposed and the time when the exposure occurred, and compensator 114 applies these signals to the radiation damage tables to generate the N radiation correction factors Rad Dam:j. The temperature and radiation compensation tables are preferably updated, for example, on the order of once a month, to insure that they remain accurate, however, it appears that these tables do not change significantly even over time scales of much longer than a month.

Since the estimates E:j generated by compensator 114 are indicative of $\int \mu dL$ for all N channels, these estimates could be directly applied to the inputs of the back projection processor 116. However, compensator 114 preferably also provides compensation for non-linearities in the detectors of array 44. Since scanner 40 uses a relatively soft X-ray beam, the response of the detectors tends to be relatively non-linear, and compensator 114 preferably provides compensation for these non-linearities.

Figure 5:
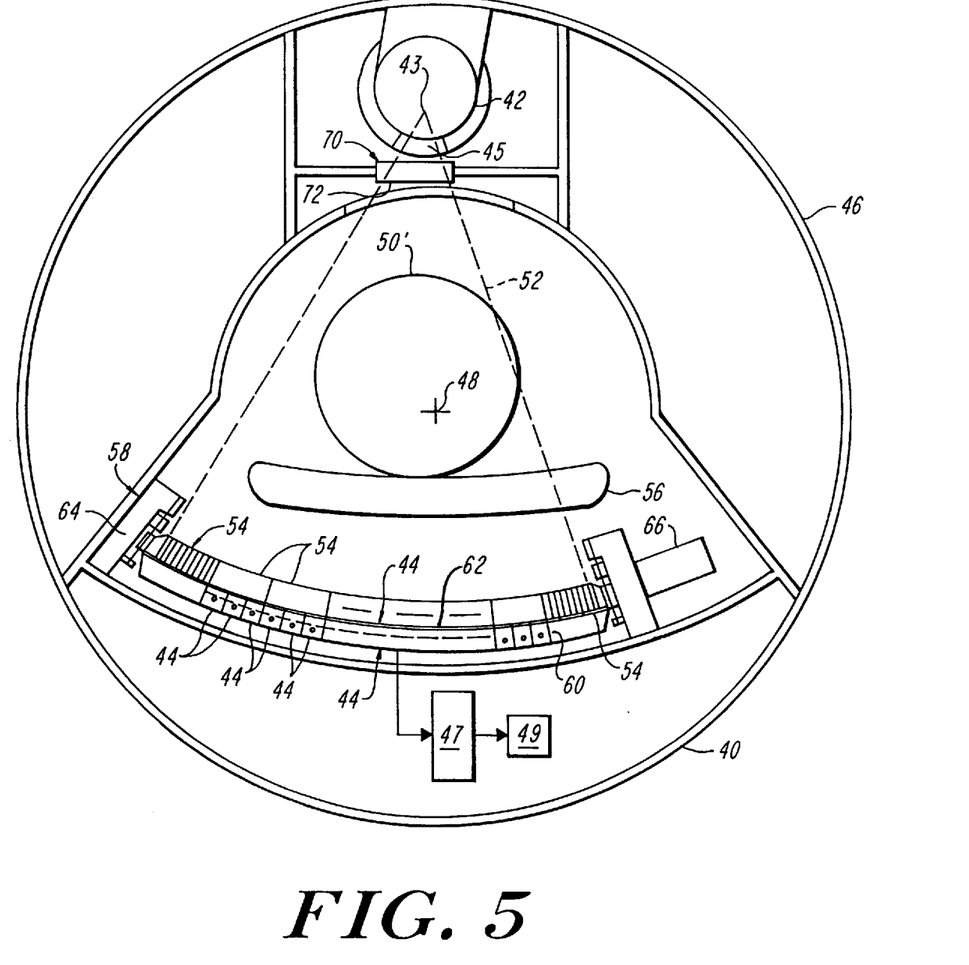
FIG. 5 is an axial view of a CT scanner constructed according to the invention with a water phantom inserted into the opening of the disk.

Compensator 114 preferably contains a set of N non-linearity compensation tables which are experimentally determined. In a preferred mode of operation, the channel dependent non-linearity compensation tables are generated by taking a series of projection views of one or more objects having a known shape and uniform density. One preferred object is a cylindrically or circularly shaped, water filled, balloon, commonly referred to as a "water phantom" or "phantom". FIG. 5 shows a water phantom 50' inserted into the opening of disk 46. The walls of phantom 50' are preferably thin so that the amount of X-rays absorbed by the walls is negligible compared to the amount of X-rays absorbed by the water contained within the phantom, and scanner 40 therefore perceives phantom 50' as a volume of water. Since phantom 50' has a known shape and is positioned at a known position within disk 46, the length of water through which a ray must travel to reach each detector in array 44 can be precalculated for all possible projection angles. Preferably, scanner 40 generates projection views at several different projection angles for one or more phantoms positioned at one or more locations so that the estimate E:j in each channel is measured for many different lengths L of water. This data is then assembled, using known statistical techniques, to generate a curve for each channel in scanner 40 relating the estimate E:j to the length of water through which the beam actually passed to generate that estimate. These curves are then stored in the non-linearity compensation tables, so that in operation during a scan, the jth estimate E:j is applied to the jth non-linearity compensation table and the output of this table is the quantity $\int \mu dL$ where $\mu$ is the coefficient of absorption for water and L is the length of water through which a ray would have had to have passed for the jth channel to have generated that estimate E:j. The non-linearity compensation tables are preferably stored in a bank of look up tables in compensator 114.

During a scan, $\mu$ is generally unknown since scanner 40 has no way of a priori determining which part of a patient (i.e., bone, fat, muscle and how much of each) is positioned between the source and a particular detector. However, since the value of $\mu$ for most types of body tissue is within 5% of the value of $\mu$ for water, it is reasonable to assume that the value of $\mu$ is that of water when generating a CT scan of a human patient.

Scanner 40 thereby provides compensation independently in each channel for errors in the detectors caused by zero offset, temperature variation, radiation damage, and non-linear behavior caused by the soft X-ray beam. By providing compensation for all of these factors, scanner 40 increases the accuracy of each channel and thereby allows X-ray source 42 to operate at reduced power levels.

Phantoms may also be used advantageously in conjunction with scanner 40 for determining an optimal thickness for the beam hardening filter. In general, the thickness of the beam hardening filter is preferably matched to a particular operating power level of the X-ray source. Once a particular operating power level is chosen, several CT images are generated of a phantom that has a density close to that of a human head (i.e., about 3.5% greater than the density of water) using beam hardening filters of varying thicknesses. Beam hardening filters that are too thick tend to decrease the quality of the CT images, so a thickness for the beam hardening filter is preferably selected by choosing the thickest filter that does not reduce the resolution of the CT images. Using a low power X-ray source and selecting the beam hardening filter in this fashion allow scanner 40 to operate at reduced power levels.

As has been described, scanner 40 uses a collection of several techniques to minimize the X-ray power requirements. This reduction in X-ray power requirements dramatically reduces the peak power requirements of scanner 40, so that the peak power requirements of scanner 40 are approximately 1.5 kVA (kilovolt-amperes) whereas most prior art CT scanners have peak power requirements in the range of 30–100 kVA. As is more fully described in copending U.S. patent application Ser. No. 08/345,493 filed Nov. 28, 1994, entitled METHOD OF AND APPARATUS FOR POWER MANAGEMENT AND DISTRIBUTION IN A MEDICAL IMAGING SYSTEM (Attorney Docket No. ANA-027), assigned to the assignee of the present invention, and which is hereby incorporated by reference, these dramatic reductions in peak power requirements enable scanner 40 to be powered by a standard 110 VAC outlet, and allow scanner 40 to include a secondary energy storage device such as a battery or a flywheel which supplies power to scanner 40 in the event that the external supply (e.g., the 110 VAC outlet) can not supply the power demands of the scanner.

While the invention has been described in connection with CT scanners of the third generation type, it should be evident to those skilled in the art that the principles of the present invention can be applied to other types of CT scanners such as fourth generation machines, where the detectors are equiangularly spaced around the periphery of the frame within which the disk and X-ray source rotate about the object being scanned.

Since certain changes may be made in the above apparatus without departing from the scope of the invention herein involved, it is intended that all matter contained in the above description or shown in the accompanying drawing shall be interpreted in an illustrative and not a limiting sense.

What is claimed is:

1. A medical computed tomography scanning system, comprising:

X-ray tomography means including (a) X-ray generating means for generating X-rays so that the X-rays emanate substantially from a focal spot, and (b) X-ray detector means for detecting at least a portion of the X-rays generated by the X-ray generating means and incident on the X-ray detection means during a tomographic scan;

a support for supporting a patient; and means for rotating at least the X-ray generating means about a rotation axis defining an isocenter of the system such that at least said X-ray generating means rotates about the support and the focal spot remains substantially at a fixed, predetermined radial distance from the isocenter during a scan;

wherein the means for generating X-rays is positioned for rotation about said rotation axis such that the focal spot is separated a substantially fixed radial distance from the isocenter by a predetermined amount sufficient to accommodate a patient but less than about 510 mm.

2. A system according to claim 1, wherein the X-ray generating means includes a source of X-rays operable at a rated power of less than about 12 kW, but sufficient to perform a scan.

3. A system according to claim 1, wherein the X-ray generating means includes an anode and a cathode, means for maintaining the anode at a potential different from the cathode and means for generating a current between the cathode and the anode so that the rated power is sufficient to perform a scan, but less than 12 kW.

4. A system according to claim 1, wherein the X-ray generating means for generating X-rays includes a filter so as to pass soft X-rays so that the energy levels of soft X-rays emanating from the focal spot and incident on the X-ray detector means between about 20 keV and about 50 keV are greater than that provided by a 0.008 inch copper filter, and less than unfiltered X-rays emanating from the focal spot.

5. A system according to claim 1, wherein the X-ray generating means for generating X-rays operates so that the X-rays emanating from the focal spot and incident on the detector means include X-ray photons having a range of energy levels, the range of energy levels having, a peak between 20 keV and 50 keV.

6. A system according to claim 1, further including a beam hardening filter disposed proximal to the X-ray generating means and between the X-ray generating means and the X-ray detector means, the beam hardening filter comprising a sheet of metal providing an X-ray photon filtering characteristic equivalent to that of a sheet of copper less than 0.008 inches thick.

7. A system according to claim 1, wherein the X-ray detector means comprises a plurality of solid state detectors.

8. A system according to claim 1, wherein said X-ray detector means comprises a plurality of detectors, said system further comprising beam defining means, mounted proximal to the focal spot, for forming a fan beam of the X-rays so that at least a portion of the fan beam is incident on the plurality of detectors, and monitoring means for maintaining the fan beam substantially incident on each of said detectors irrespective of any displacement of said focal spot in a direction parallel to the rotation axis.

9. A system according to claim 8, wherein said X-ray detector means comprises an array of detectors, and the monitoring means includes (a) means for sensing a displacement of the focal spot in a direction parallel to the rotation axis, and (b) means for shifting the beam defining means so as to maintain the fan beam substantially incident on the same portion of the array of detectors.

10. A system according to claim 1, wherein said X-ray detector means comprises a plurality of detectors, and further comprising best estimate filter means for filtering the output signals generated by the plurality of X-ray detectors.

11. A system according to claim 1, wherein said X-ray detector means comprises a plurality of detectors, and further comprising calibration means for compensating for a non-linearity of the signal output of each of the detectors.

12. A system according to claim 1, wherein said X-ray detector means comprises a plurality of detectors, and further comprising calibration means for compensating for variations among the detectors.

13. A system according to claim 1, wherein the means for generating X-rays is positioned for rotation about said rotation axis such that the focal spot is separated a substantially fixed radial distance from the isocenter by less than about 510 mm, but greater than a distance on the order of 450 mm.

14. A system according to claim 1, wherein the X-ray generating means includes a source of X-rays operable at a rated power of less than about 12 kW, but greater than a power level on the order of 1 kW.

15. A system according to claim 1, wherein the X-ray generating means includes a source of X-rays operable so that said source uses on the order of 100 mAs per scan.

16. A medical computed tomography system, comprising: X-ray tomography means including (a) X-ray generating means for generating X-rays, and (b) X-ray detector means for detecting at least a portion of the X-rays generated by the X-ray generating means and incident on the X-ray detection means during a tomographic scan;

a support for supporting a patient; and means for rotating at least the X-ray generating means about a rotation axis such that said X-ray generating means rotates about said support;

wherein the X-ray generating means includes a source of X-rays operable at a rated power less than 12 kW, but sufficient to perform a 360 degree scan in a time period on the order of two seconds.

17. A system according to claim 16, wherein the X-ray detectors comprise solid state detectors.

18. A system according to claim 16, wherein said X-ray generating means for generating X-rays generates the X-rays so that the X-rays emanate substantially from a focal spot and said X-ray detector means comprises a plurality of detectors, said system further comprising beam defining means, mounted proximal to the focal spot, for forming a fan beam of the X-rays so that at least a portion of the fan beam is incident on the plurality of detectors, and monitoring means for maintaining the fan beam substantially incident on each of said detectors irrespective of any displacement of said focal spot in a direction parallel to the rotation axis.

19. A system according to claim 18, wherein the monitoring means includes (a) means for sensing a displacement of the focal spot in a direction parallel to the rotation axis, and (b) means for shifting the beam defining means so as to maintain the fan beam substantially incident on the same portion of the array of detectors.

20. A system according to claim 16, wherein said X-ray detector means comprises a plurality of detectors, and further comprising best estimate filter means for filtering the output signals generated by the plurality of X-ray detectors.

21. A system according to claim 16, wherein said X-ray detector means comprises a plurality of detectors, and further comprising calibration means for compensating for a non-linearity of the signal output of each of the detectors.

22. A system according to claim 16, wherein said X-ray detector means comprises a plurality of detectors, and further comprising calibration means for compensating for variations among the detectors.

23. A system according to claim 16, wherein the X-ray generating means for generating X-rays operates so that the energy levels of soft X-ray photons generated by the X-ray generating means and incident on the X-ray detector means between about 20 keV and about 50 keV are greater than that provided by a 0.008 inch copper filter, and less than unfiltered X-rays generated by the X-ray generating means.

24. A system according to claim 16, wherein the X-rays generated by the X-ray generating means and incident on the detector means include X-ray photons having a range of energy levels, the range of energy levels having a peak between 20 keV and 50 keV.

25. A system according to claim 16, further including a beam hardening filter disposed proximal to the X-ray generating means and between the X-ray generating means and the X-ray detector means, the beam hardening filter comprising a sheet of metal providing an X-ray photon filtering characteristic equivalent to that of a sheet of copper less than 0.008 inches thick.

26. A medical computed tomography system, comprising: X-ray tomography means including (a) X-ray generating means for generating X-rays, and (b) X-ray detector means for detecting at least a portion of the X-rays generated by the X-ray generating means and incident on the X-ray detection means during a tomographic scan;

a support for supporting a patient; and means for rotating at least the X-ray generating means about a rotation axis such that said X-ray generating rotates about said support;

wherein the X-ray generating means for generating X-rays includes a source of X-rays and a filter so as to pass soft X-rays so that the energy levels of soft X-ray photons generated by said X-ray generating means and incident on the X-ray detector means between about 20 keV and about 50 keV are greater than that provided by a 0.008 inch copper filter and less than unfiltered X-rays generated by said source of X-rays.

27. A system according to claim 26, wherein the X-ray generating means for generating X-rays operates so that X-ray photons generated by said X-ray generating means and incident on the X-ray detector means include X-ray photons having a range of energy levels, the range of energy levels having a peak between 20 keV and 50 keV.

28. A system according to claim 26, further including a beam hardening filter disposed proximal to the X-ray generating means and between the X-ray generating means and the X-ray detector means, the beam hardening filter comprising a sheet of metal providing an X-ray photon filtering characteristic equivalent to that of a sheet of copper less than 0.008 inches thick.

29. A medical computed tomography system, comprising:
X-ray tomography means including (a) X-ray generating means for generating X-rays, and (b) X-ray detector means for detecting at least a portion of the X-rays generated by the X-ray generating means and incident on the X-ray detection means during a tomographic scan;
means for rotating at least the X-ray generating means about a rotation axis;
a support for supporting a patient; and
a beam hardening filter disposed proximal to the X-ray generating means and between the X-ray generating means and the X-ray detector means, the beam hardening filter comprising a sheet of metal providing an X-ray photon filtering characteristic equivalent to that of a sheet of copper less than 0.008 inches thick.

30. A system according to claim 29, wherein the X-ray detector means includes a plurality of solid state detectors.

31. A system according to claim 29, wherein said X-ray generating means for generating X-rays generates the X-rays so that the X-rays emanate substantially from a focal spot and said X-ray detector means comprises a plurality of detectors, said system further comprising beam defining means, mounted proximal to the focal spot, for forming a fan beam of the X-rays so that at least a portion of the fan beam is incident on the plurality of detectors, and monitoring means for maintaining the fan beam substantially incident on each of said detectors irrespective of any displacement of said focal spot in a direction parallel to the rotation axis.

32. A system according to claim 31, wherein the monitoring means includes (a) means for sensing a displacement of the focal spot in a direction parallel to the rotation axis, and (b) means for shifting the beam defining means so as to maintain the fan beam substantially incident on the same portion of the array of detectors.

33. A system according to claim 29, wherein said X-ray detector means comprises a plurality of detectors, and further comprising calibration means for compensating for variations among the detectors.

34. A system according to claim 29, wherein said X-ray detector means comprises a plurality of detectors, and further comprising calibration means for compensating for a non-linearity of the signal output of each of the detectors.

35. A system according to claim 29, wherein said X-ray detector means comprises a plurality of detectors, and further comprising best estimate filter means for filtering the output signals generated by the plurality of X-ray detectors.

36. A medical computed tomography system, comprising:
X-ray tomography means including (a) X-ray generating means for generating X-rays, and (b) X-ray detector means for detecting at least a portion of the X-rays generated by the X-ray generating means and incident on the X-ray detection means during a tomographic scan;
a support for supporting a patient; and
means for rotating at least the X-ray generating means about a rotation axis such that said X-ray generating means rotates about said support;
wherein the X-ray generating means includes a source of X-rays operable on the order of 100 mAs per scan.

37. A system according to claim 36, wherein the X-ray generating means for generating X-rays operates so that the energy levels of soft X-ray photons generated by the X-ray generating means and incident on the X-ray detector means between about 20 keV and about 50 keV are greater than that provided by a 0.008 inch copper filter and less than unfiltered X-rays generated by the X-ray generating means.

38. A system according to claim 36, wherein the X-rays generated by the X-ray generating means and incident on the detector means include X-ray photons having a range of energy levels, the range of energy levels having a peak between 20 keV and 50 keV.

39. A method of performing a medical computed tomography scan, comprising:
supporting a patient; and
during a scan, rotating an X-ray source about a rotation axis such that said X-ray source rotates about the patient and operating the X-ray source at a rate on the on the order of 100 mAs per scan.

40. A method according to claim 39, wherein the step of operating the X-ray source includes the step of generating X-rays so that the energy levels of soft X-ray photons generated by the X-ray source and incident on an array of detectors between about 20 keV and about 50 keV are greater than that provided by a 0.008 inch copper filter and less than unfiltered X-rays generated by the X-ray source.

41. A method according to claim 39, wherein the step of operating the X-ray source includes the step of generating X-ray photons having a range of energy levels, the range of energy levels having a peak between 20 keV and 50 keV.

42. A method of performing a medical computed tomography scan, comprising:
supporting a patient; and
rotating at least an X-ray source having a focal spot about a rotation axis so as to define an isocenter such that (a) at least the X-ray source rotates about the patient and the focal spot remains substantially at a fixed, predetermined radial distance from the isocenter during a scan, and (b) the focal spot is separated a substantially fixed radial distance from the isocenter by a predetermined amount sufficient to accommodate a patient, but less than about 510 mm.

43. A method according to claim 42, further including the step of operating the X-ray source at a rated power of less than about 12 kW, but sufficient to perform a scan.

44. A method according to claim 42, wherein the X-ray source includes an anode and a cathode, further including the steps of
maintaining the anode at a potential different from the cathode; and
generating a current between the cathode and the anode so that the rated power is sufficient to perform a scan, but less than 12 kW.

45. A method according to claim 42, wherein the X-ray source includes a filter so as to pass soft X-rays so that the energy levels of soft X-rays emanating from the focal spot and incident on an array of X-ray detectors between about 20 keV and about 50 keV are greater than that provided by a 0.008 inch copper filter, and less than unfiltered X-rays emanating from the focal spot.

46. A method according to claim 42, wherein the X-rays emanating from the focal spot and incident on the detectors include X-ray photons having a range of energy levels, the range of energy levels having a peak between 20 keV and 50 keV.

47. A method according to claim 42, further including the step of disposing a beam hardening filter proximal to the X-ray source and between the X-ray source and an array of X-ray detectors, the beam hardening filter comprising a sheet of metal providing an X-ray photon filtering characteristic equivalent to that of a sheet of copper less than 0.008 inches thick.

48. A method according to claim 42, further comprising the steps of forming a fan beam of the X-rays so that at least a portion of the fan beam is incident on an array of detectors, and monitor the position of the fan beam relative to the rotation axis for maintaining the fan beam substantially incident on each of the detectors irrespective of any displacement of the focal spot in a direction parallel to the rotation axis.

49. A method according to claim 48, wherein the step of monitoring includes (a) sensing a displacement of the focal spot in a direction parallel to the rotation axis, and (b) shifting a beam defining subsystem so as to maintain the fan beam substantially incident on the same portion of the array of detectors.

50. A method according to claim 42, further comprising the step of filtering each of the output signals generated by the plurality of X-ray detectors with a best estimate filter.

51. A method according to claim 42, further comprising the step of compensating for a non-linearity of the signal output of each of the detectors.

52. A method according to claim 42, further comprising the step of compensating for variations in responses of detectors of an array of detectors positioned to receive X-rays from the X-ray source.

53. A method of performing a medical computed tomography scan, comprising:

supporting a patient; and scanning the patient with an X-ray beam while filter the X-ray beam with a beam hardening filter comprising a sheet of metal providing an X-ray photon filtering characteristic equivalent to that of a sheet of copper less than 0.008 inches thick.

54. A method of performing a medical computed tomography scan, comprising:

supporting a patient; and rotating the X-ray source about a rotation axis such that the X-ray source rotates about the patient, and generates soft X-rays so that the energy levels of soft X-ray photons generated by said X-ray source and incident on an array of X-ray detectors between about 20 keV and about 50 keV are greater than that provided by a 0.008 inch copper filter and less than unfiltered X-rays generated by said source of X-rays.

55. A method according to claim 54, the soft X-rays generated by the X-ray source and incident on the X-ray detector means include X-ray photons having a range of energy levels, the range of energy levels having a peak between 20 keV and 50 keV.

56. A method according to claim 54, further including the step of filtering the X-rays with a beam hardening filter, wherein the beam hardening filter provides an X-ray photon filtering characteristic equivalent to that of a sheet of copper less than 0.008 inches thick.

57. A method of performing a medical computed tomography scan, comprising:

supporting a patient; and rotating at least the X-ray source about a rotation axis such that the X-ray source rotates about the patient and the X-ray source is operated at a rated power less than 12 kW, but sufficient to perform a 360 degree scan in a time period on the order of two seconds.

58. A method according to claim 57, wherein the X-ray source is operated so that the energy levels of soft X-ray photons generated by the X-ray source and incident on an array of X-ray detectors between about 20 keV and about 50 keV are greater than that provided by a 0.008 inch copper filter, and less than unfiltered X-rays generated by the X-ray source.

59. A method according to claim 57, wherein the X-rays generated by the X-ray source and incident on an array of detectors includes X-ray photons having a range of energy levels, the range of energy levels having a peak between 20 keV and 50 keV.

60. A method according to claim 57, further including the step of positioning proximal to the X-ray generating means and between the X-ray source and an array of X-ray detectors, a beam hardening filter comprising a sheet of metal providing an X-ray photon filtering characteristic equivalent to that of a sheet of copper less than 0.008 inches thick.

61. A method according to claim 57, wherein the X-ray source generates X-rays so that the X-rays emanate substantially from a focal spot, said method further comprising the step of forming a fan beam of the X-rays emanating from the focal spot so that at least a portion of the fan beam is incident on a plurality of detectors, and maintaining the fan beam substantially incident on each of the detectors irrespective of any displacement of the focal spot in a direction parallel to the rotation axis.

62. A method according to claim 61, wherein the step of maintaining the fan beam substantially incident includes the steps of (a) sensing a displacement of the focal spot in a direction parallel to the rotation axis, and (b) shifting the fan beam so as to maintain the fan beam substantially incident on the same portion of the plurality of detectors.

63. A method according to claim 57, wherein a plurality of X-ray detectors are positioned to receive X-rays emanating from the X-ray source during a scan, further including the step of filtering each of the output signals of the X-ray detectors with a plurality of best estimate filters.

64. A method according to claim 63, further including the step of compensating for a non-linearity of the signal output of each of the detectors.

65. A method according to claim 63, further including the step of compensating for variations in the responses of the detectors.

* * * * *

UNITED STATES PATENT AND TRADEMARK OFFICE
CERTIFICATE OF CORRECTION

PATENT NO.: 5,867,553

DATED: February 2, 1999

INVENTOR(S): Bernard M. Gordon et al.

It is certified that error appears in the above-identified patent and that said Letters Patent is hereby corrected as shown below:

Claim 39, column 20, line 29, delete "on the".

Signed and Sealed this

Twenty-second Day of June, 1999

*Attest:*

Q. TODD DICKINSON

*Attesting Officer*   *Acting Commissioner of Patents and Trademarks*